US00PP36392P2

(12) United States Plant Patent
Schreurs

(10) Patent No.: US PP36,392 P2
(45) Date of Patent: Jan. 14, 2025

(54) ***GERBERA* PLANT NAMED 'GOS202101'**

(50) Latin Name: *Gerbera hybrida*
Varietal Denomination: GOS202101

(71) Applicant: PIET SCHREURS HOLDING B.V., De Kwakel (NL)

(72) Inventor: Petrus N. J. Schreurs, De Kwakel (NL)

(73) Assignee: PIET SCHREURS HOLDING B.V., DeKwakel (NL)

( * ) Notice: Subject to any disclaimer, the term of this patent is extended or adjusted under 35 U.S.C. 154(b) by 0 days.

(21) Appl. No.: 18/600,699

(22) Filed: Mar. 9, 2024

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./357
CPC ..... A01H 5/02; A01H 5/00; A01H 6/1456; A01H 6/14
See application file for complete search history.

(56) References Cited

U.S. PATENT DOCUMENTS

PP27,962 P2 * 5/2017 Moen ..... A01H 5/02 Plt./357

* cited by examiner

*Primary Examiner* — June Hwu
(74) *Attorney, Agent, or Firm* — C. Anne Whealy

(57) ABSTRACT

A new and distinct cultivar of *Gerbera* plant named 'GOS202101', characterized by its broadly upright and uniformly mounding plant habit; vigorous growth habit and rapid growth rate; dense and bushy appearance; numerous large double type inflorescences with purplish red and white bi-colored florets; upright and moderately strong peduncles; and good garden performance and relative tolerance to low temperatures.

2 Drawing Sheets

Figure 1:
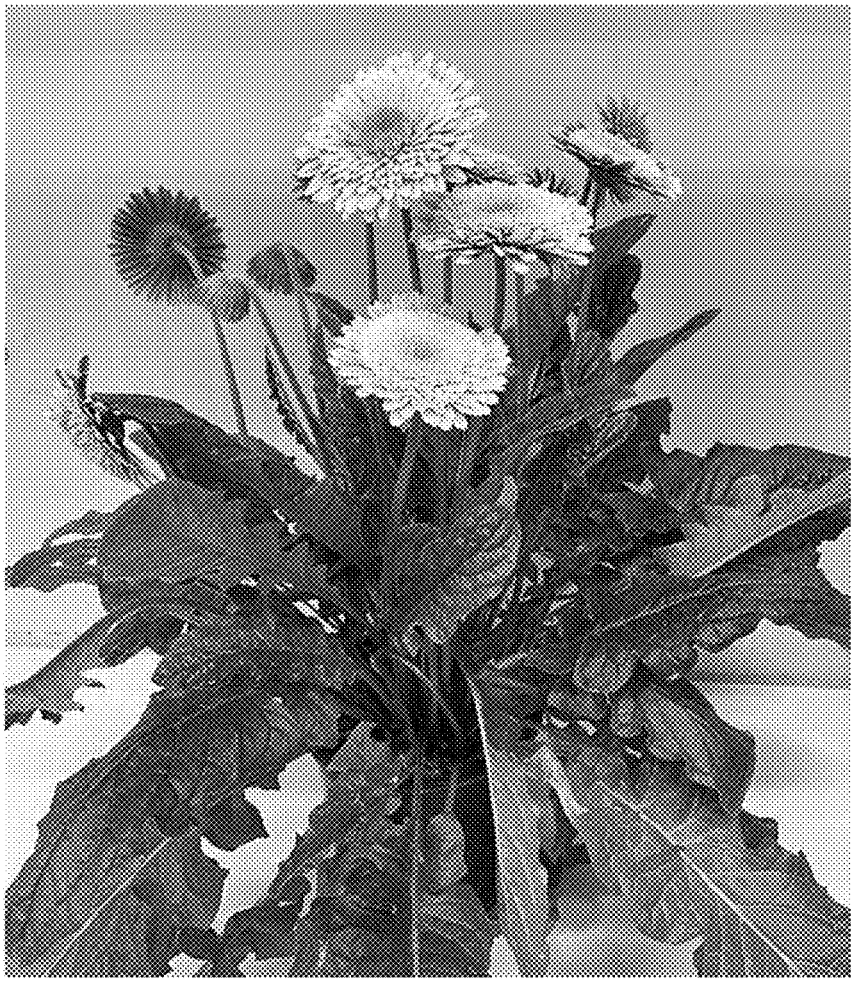

Botanical designation: *Gerbera hybrida.*
Cultivar denomination: 'GOS202101'.

BACKGROUND OF THE INVENTION

The present invention relates to a new and distinct cultivar of *Gerbera* plant, botanically known as *Gerbera hybrida* and hereinafter referred to by the cultivar name 'GOS202101'.

The new *Gerbera* plant is a product of a planned breeding program conducted by the Inventor in De Kwakel, The Netherlands. The objective of the breeding program is to create new garden *Gerbera* plants with numerous attractive double type inflorescences, resistance to low temperatures and good garden performance.

The new *Gerbera* plant originated from a cross-pollination in September 2020 of a proprietary selection of *Gerbera hybrida* identified as code number GO 1394, not patented, as the female, or seed, parent with a proprietary selection of *Gerbera hybrida* identified as code number GO 1675, not patented, as the male, or pollen, parent. The new *Gerbera* plant was discovered and selected as a single flowering plant from within the progeny of the stated cross-pollination in a controlled greenhouse environment in De Kwakel, The Netherlands in August 2021.

Asexual reproduction of the new *Gerbera* plant by vegetative terminal cuttings since February 2022 in a controlled environment in De Kwakel, The Netherlands, has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GOS202101'. These characteristics in combination distinguish 'GOS202101' as a new and distinct *Gerbera* plant:

1. Broadly upright and uniformly mounding plant habit.
2. Vigorous growth habit and rapid growth rate.
3. Dense and bushy appearance.
4. Numerous large double type inflorescences with purplish red and white bi-colored florets.
5. Upright and moderately strong peduncles.
6. Good garden performance and relative tolerance to low temperatures.

Plants of the new *Gerbera* differ primarily from plants of the female parent selection in the following characteristics:

1. Plants of the new *Gerbera* have larger inflorescences than plants of the female parent selection.
2. Plants of the new *Gerbera* have smaller ray florets than plants of the female parent selection.

Plants of the new *Gerbera* differ primarily from plants of the male parent selection in the following characteristics:

1. Plants of the new *Gerbera* have narrower leaves than plants of the male parent selection.

2. Inflorescences of plants of the new *Gerbera* are double types whereas inflorescences of plants of the male parent selection are semi-double types.

Plants of the new *Gerbera* can be compared to plants of the *Gerbera hybrida* 'Garsurprise', disclosed in U.S. Plant Pat. No. 27,962. In side-by-side comparisons, plants of the new *Gerbera* differ from plants of 'Garsurprise' in the following characteristics:

1. Plants of the new *Gerbera* have larger inflorescences than plants of 'Garsurprise'.
2. Inflorescences of plants of the new *Gerbera* are double types whereas inflorescences of plants of 'Garsurprise' are single types.
3. Florets of plants of the new *Gerbera* are purplish red and white bi-colored whereas florets of plants of 'Garsurprise' are dark red purple in color.

BRIEF DESCRIPTION OF THE PHOTOGRAPHS

The accompanying photographs illustrate the overall appearance of the new *Gerbera* plant showing the colors as true as it is reasonably possible to obtain in colored reproductions of this type. Colors in the photographs may differ slightly from the color values cited in the detailed botanical description which accurately describe the colors of the new *Gerbera* plant.

The photograph on the first sheet (FIG. 1) is a side perspective view of a typical flowering plant of 'GOS202101' grown in a container.

Figure 2:
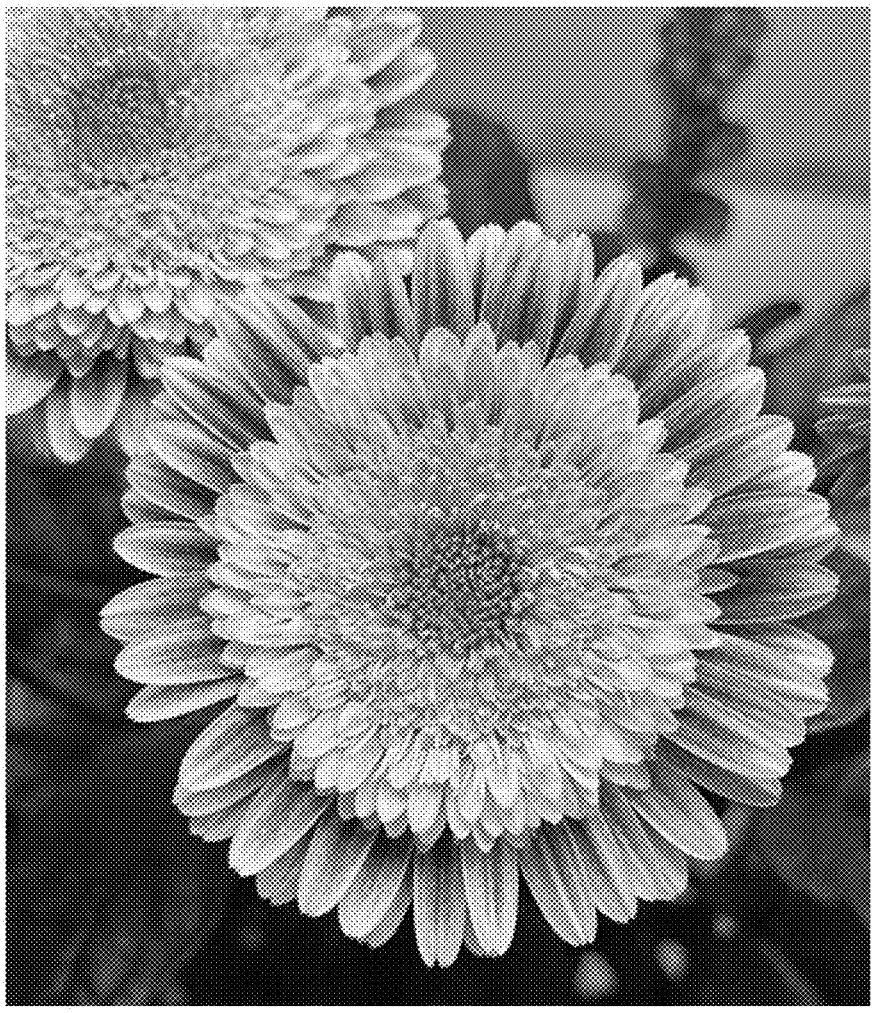

The photograph on the second sheet (FIG. 2) is a close-up view of typical inflorescences of 'GOS202101'.

DETAILED BOTANICAL DESCRIPTION

The aforementioned photographs and following observations and measurements describe plants grown during the winter in 19-cm containers in a glass-covered greenhouse in De Kwakel, The Netherlands and under cultural practices typical of commercial garden *Gerbera* production. During the production of the plants, day temperatures ranged from 16° C. to 18° C. and night temperatures ranged from 10° C. to 11° C. Plants were five months old when the photographs and description were taken. In the following description, color references are made to The Royal Horticultural Society Colour Chart, 2015 Edition, except where general terms of ordinary dictionary significance are used.

Botanical classification: *Gerbera hybrida* 'GOS202101'.

Parentage:

*Female, or seed, parent*.—Proprietary selection of *Gerbera hybrida* identified as code number GO 1394, not patented.

*Male, or pollen, parent*.—Proprietary selection of *Gerbera hybrida* identified as code number GO 1675, not patented.

Propagation:

*Type*.—By vegetative cuttings.

*Time to initiate roots, summer*.—About 2.5 to 3 weeks at temperatures about 20° C. to 25° C.

*Time to initiate roots, winter*.—About 3 to 3.5 weeks at temperatures about 16° C. to 18° C.

*Time to produce a rooted young plant, summer*.—About four weeks at temperatures about 20° C. to 25° C.

*Time to produce a rooted young plant, winter*.—About five to six weeks at temperatures about 16° C. to 18° C.

*Root description*.—Fibrous; medium in thickness; typically white in color, actual color of the roots is dependent on substrate composition, water quality, fertilizer type and formulation, substrate temperature and physiological age of roots.

*Rooting habit*.—Freely branching; medium density.

Plant description:

*Appearance*.—Herbaceous perennial that is typically grown as a garden plant; broadly upright and uniformly mounding; roughly flattened globular in shape; numerous leaves arranged in basal rosettes; dense and bushy plant habit; inflorescences held above the foliar plane on erect and moderately strong basal peduncles; vigorous growth habit and rapid growth rate.

*Plant height, soil level to top of foliar plane*.—About 37.6 cm.

*Plant height, soil level to top of inflorescences*.—About 56.9 cm.

*Plant width or spread*.—About 76.6 cm.

Leaf description:

*Arrangement*.—Alternate, basal, simple.

*Length*.—About 31 cm.

*Width*.—About 11.8 cm.

*Shape*.—Narrowly obovate to narrowly ovate in overall outline.

*Apex*.—Obtuse.

*Base*.—Attenuate to broadly attenuate.

*Margin*.—Coarsely angulate; proximally, coarsely and irregularly angulate to runcinate; moderately undulate to coarsely repand; sinuses parallel to divergent and shallow to deep.

*Texture and luster, upper surface*.—Glabrous to sparsely pubescent; slightly to moderately glossy.

*Texture and luster, lower surface*.—Moderately pubescent, slightly glossy.

*Venation pattern*.—Pinnate.

*Color*.—Developing leaves, upper surface: Close to 143A. Developing leaves, lower surface: Close to a blend of 144A and 146B. Fully expanded leaves, upper surface: Close to NN137A; venation, close to 144A. Fully expanded leaves, lower surface: Close to 147B; venation, close to 144A.

*Petioles*.—Length: About 14.7 cm. Diameter: About 4.5 mm. Texture and luster, upper and lower surfaces: Moderately pubescent; moderately glossy. Strength: Moderately strong to strong. Color, upper surface: Close to 144A; towards the margins, close to 148A; towards the base, close to 176B. Color, lower surface: Close to 144A; towards the base, close to 176B.

Inflorescence description:

*Appearance*.—Composite double type inflorescence form with oblanceolate-shaped ray florets; solitary inflorescences borne on upright and moderately strong peduncles and held above the foliar plane; ray and disc florets arranged acropetally on a capitulum; inflorescences face mostly upright.

*Fragrance*.—None detected.

*Flowering season*.—Plants begin flowering about 1.5 months after planting; under garden conditions in The Netherlands, plants flower from late spring into the autumn; plants can be flowered year-round in the greenhouse.

*Inflorescence longevity*.—Depending on the temperature, inflorescences last about three to four weeks on the plant; inflorescences persistent.

*Quantity of inflorescences*.—Freely flowering habit with at least 13 developing and open inflorescences per plant at one time.

*Inflorescence buds*.—Height: About 2.2 cm. Diameter: About 5 cm. Shape: Broadly inverted triangular. Texture and luster: Moderately to densely pubescent; matte. Color, immature involucral bracts: Close to 138A; towards the apex, close to a blend of 138A and 138B. Color, immature ray florets: Close to 149C tinged with close to 176B.

*Inflorescence size*.—Diameter: About 9.2 cm. Depth (height): About 2.8 cm. Diameter of disc: About 7 cm.

*Receptacles*.—Height: About 3 mm. Diameter: About 8 mm. Shape: Disc-shaped. Color: Close to 157D.

*Ray florets*.—Quantity and arrangement: About 60 per inflorescence arranged in two whorls. Orientation: Proximally, about 40° From vertical; mostly horizontal to distally, slightly curved downward. Length: About 3.5 cm to 4.1 cm. Width: About 7 mm to 8 mm. Shape: Oblanceolate with two linear lateral lobes that are about 1.7 cm in length and about 1 mm in width. Apex: Shallowly emarginate to shallowly praemorse; lateral lobes, narrowly acute. Base: Narrowly cuneate. Margin: Entire; not undulate. Texture and luster, upper surface: Smooth, glabrous; velvety; matte. Texture and luster, lower surface: Smooth, glabrous; slightly velvety; slightly glossy. Color: When opening, upper surface: Proximally, close to 61C and distally, close to 155C and at the apex, close to 157C; lateral lobes, proximally, close to 61C and distally, close to 155C. When opening, lower surface: Proximally, close to 60B and distally, close to 144C and at the apex, close to 143C; lateral lobes, proximally, close to N66C and distally, close to 69D. Fully opened, upper surface: Proximally, close to N57A and distally, close to 155A; lateral lobes, proximally, close to N57C and distally, close to 155A; color does not change with subsequent development. Fully opened, lower surface: Proximally, close to 61A and distally, close to 58A; lateral lobes, proximally, close to 63A and distally, close to 69D; color does not change with subsequent development.

*Disc florets*.—Quantity and arrangement: About 320 disc florets arranged at center of the inflorescence in a twelve-whorl spiral; disc florets three-lobed with a central ray floret-like lobe and two narrow lateral lobes; with development, disc florets become conspicuously larger resembling the ray florets and differing in color with maturity. Central lobe: Length, fully mature: About 2 cm to 3.3 cm. Width, fully mature: About 3 mm to 5 mm. Shape: Oblanceolate. Apex: Obtuse to shallowly emarginate. Base: Fused. Margin: Entire; not undulate. Texture, upper surface: Smooth, glabrous; moderately velvety; matte. Texture, lower surface: Smooth, glabrous; slightly velvety; slightly glossy. Color: When opening, upper surface: Close to 2D; apex, slightly lighter than 146D. When opening, lower surface: Close to 1D; apex, slightly lighter than 146D. Fully opened, upper surface: Close to 61B to 61C; towards the apex, close to NN155A; at the base, close to 157C; with subsequent development, proximal color becoming closer to 61B to 61D and distally, close to 2D. Fully opened, lower surface: Close to 2D; apex, close to 154D; towards the base, close to 61B and at the base, close to 157C; color does not change with subsequent development. Lateral lobes: Length, fully mature: About 1.4 cm to 2 cm. Width, fully mature: About 5 mm to 10 mm. Shape: Linear. Apex: Acute. Base: Fused. Margin: Entire; not undulate. Texture, upper surface: Smooth, glabrous; moderately velvety; matte. Texture, lower surface: Smooth, glabrous; slightly velvety; slightly glossy. Color: When opening, upper surface: Close to 2D. When opening, lower surface: Close to 1D. Fully opened, upper surface: Close to NN155B and towards the base, tinged with close to 61D; with subsequent development, proximally, close to 61C and 61D and distally, close to 2D to lighter than 2D. Fully opened, lower surface: Close to 2D; towards the base, slightly tinged with close to 61D; color does not change with subsequent development.

*Pappus*.—Quantity of hairs per floret: Numerous. Length: About 7 mm. Diameter: Fine, less than 1 mm. Texture and luster: Soft; matte. Color: Close to 157B.

*Phyllaries*.—Quantity and arrangement: About 80 per inflorescence arranged in about three whorls. Length: About 1.7 cm. Width (at base): About 2.5 mm. Shape: Linear. Apex: Narrowly acute. Base: Cuneate. Margin: Entire. Texture and luster, upper surface: Smooth, glabrous; slightly glossy. Texture and luster, lower surface: Moderately to densely pubescent; matte. Color, upper surface: Close to 144A; main vein, close to 143A. Color, lower surface: Close to 138A; towards the apex, close to a blend of 138A and 138B.

*Peduncles*.—Length: About 52.7 cm. Diameter: Proximally, about 7 mm and distally, about 5 mm. Strength: Moderately strong. Angle: About 20° From vertical. Texture and luster: Moderately to densely pubescent; slightly glossy. Color: Close to 144A and distally, close to 143A; surfaces exposed to direct sunlight, tinged with close to 152A and 152B.

*Reproductive organs*.—Androecium (present on disc florets only): Quantity per floret: Five. Filament length: About 7 mm. Filament color: Close to 155C. Anther shape: Linear; basifixed. Anther size: About 0.3 mm by 4 mm. Anther color: Close to N199C. Pollen amount: None observed. Gynoecium (present on ray and disc florets): Quantity per floret: One. Pistil length: About 1.1 cm. Stigma diameter: About 0.3 mm. Stigma shape: Cleft. Stigma color: Close to NN155A. Style length: About 1 cm. Style color: Close to NN155A. Ovary color: Close to 157D.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −6° C. to about 35° C. and to be cold hardy to USDA Hardiness Zone 9.

It is claimed:

1. A new and distinct *Gerbera* plant named 'GOS202101' as illustrated and described.

* * * * *